United States Patent [19]

Weber et al.

[11] 4,135,254
[45] Jan. 23, 1979

[54] PROSTHETIC KNEE APPARATUS

[75] Inventors: T. Jerome Weber, Mountain View; Roy D. Roberts, San Jose, both of Calif.

[73] Assignee: Hosmer/Dorrance Corporation, Campbell, Calif.

[21] Appl. No.: 806,159

[22] Filed: Jun. 13, 1977

[51] Int. Cl.² .......................... A61F 1/04; A61F 1/08
[52] U.S. Cl. .................................................. 3/26; 3/28; 3/29
[58] Field of Search .................................. 3/22, 26–29

[56] References Cited

U.S. PATENT DOCUMENTS

| | | | |
|---|---|---|---|
| 2,645,779 | 7/1953 | Barghausen | 3/28 |
| 2,667,644 | 2/1954 | Johnson | 3/27 X |
| 2,794,987 | 6/1957 | Oliver | 3/26 |
| 2,830,301 | 4/1958 | Schober | 3/27 |
| 3,309,715 | 3/1967 | Nader et al. | 3/27 |
| 3,663,967 | 5/1972 | Vermillion | 3/26 |
| 4,005,496 | 2/1977 | Wilkes | 3/27 |
| 4,023,215 | 5/1977 | Moore | 3/26 |
| 4,064,569 | 12/1977 | Campbell | 3/26 |

FOREIGN PATENT DOCUMENTS 665403  6/1963  Canada .................................. 3/26

Primary Examiner—E. H. Eickholt
Attorney, Agent, or Firm—Harris Zimmerman

[57] ABSTRACT

A prosthetic knee apparatus includes a pair of spaced side brackets depending from the upper leg prosthesis, and a housing disposed between the brackets. Extending through the housing to the brackets are anterior and posterior pivot shafts, the posterior pivot being provided with some play to permit a slight degree of pivot about the anterior shaft. A pair of leg brackets are also joined to the posterior pivot shaft with no play, and the housing is provided with a locking pin arrangement to releasably lock the leg brackets to the housing. The housing is provided with a pair of opposed braking pads which impinge on the leg brackets, the braking pads being actuated by a wedge which is driven into engagement by weight applied to the upper leg portion posteriorly of the anterior pivot shaft.

23 Claims, 7 Drawing Figures

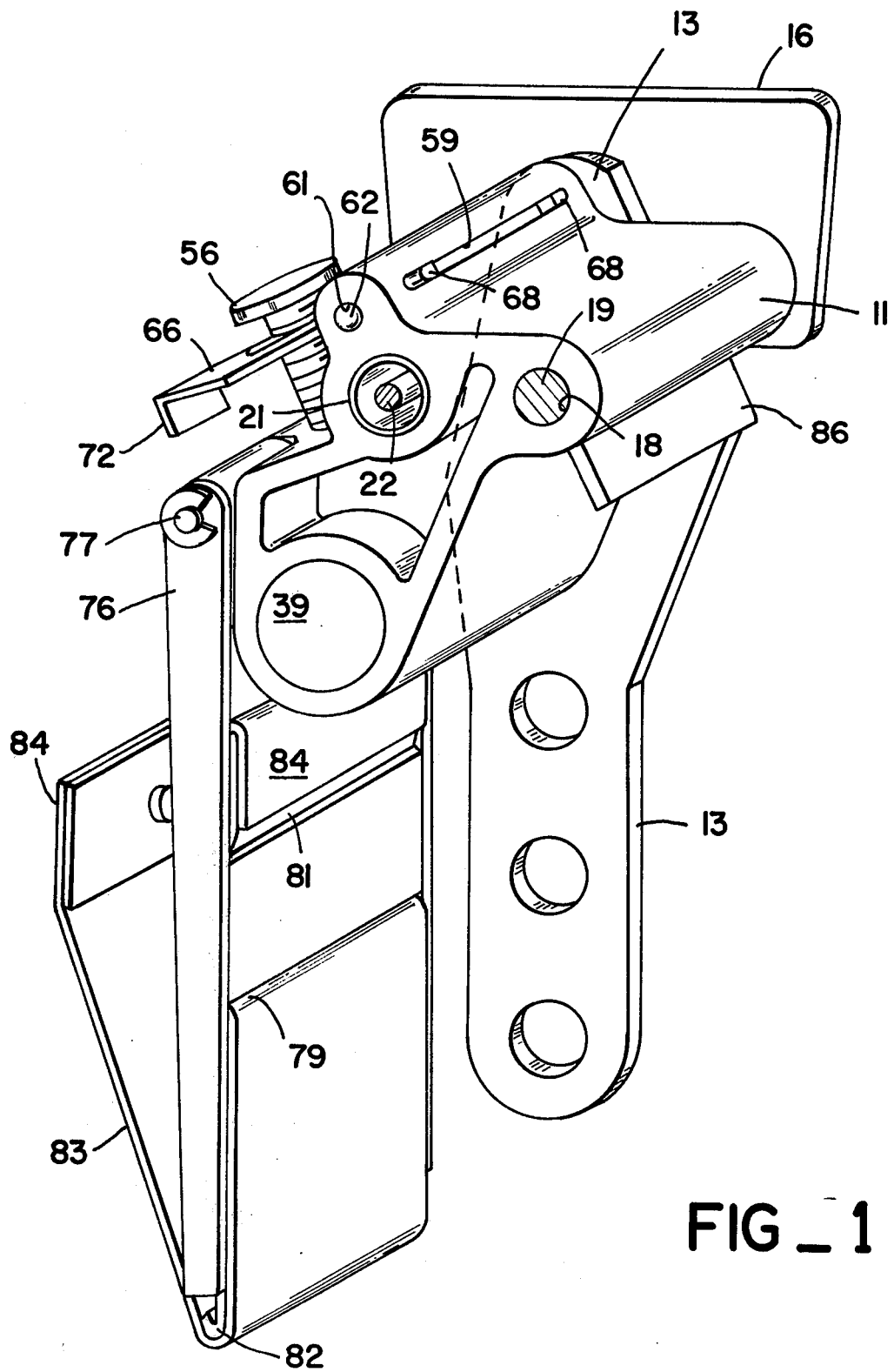
FIG_1

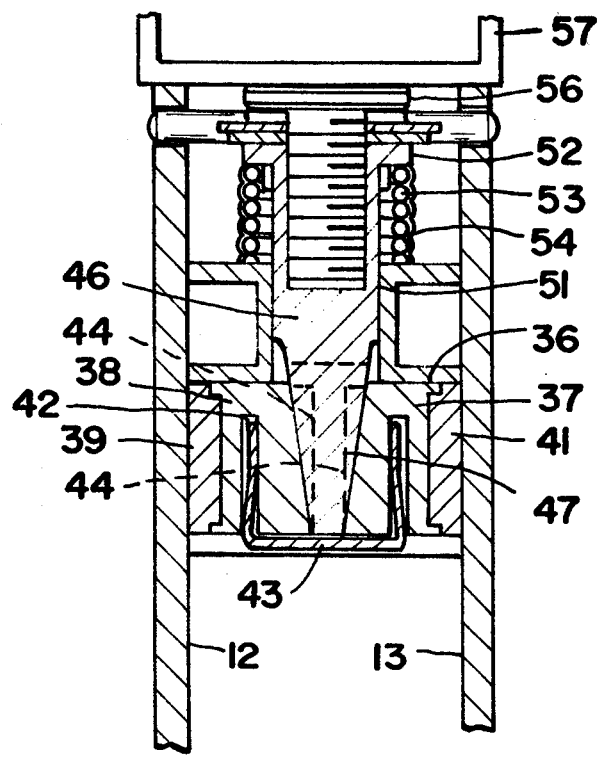
FIG_4
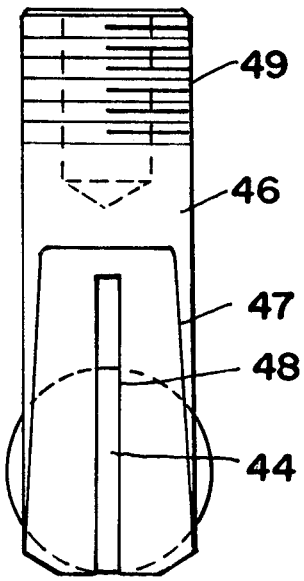
FIG_2
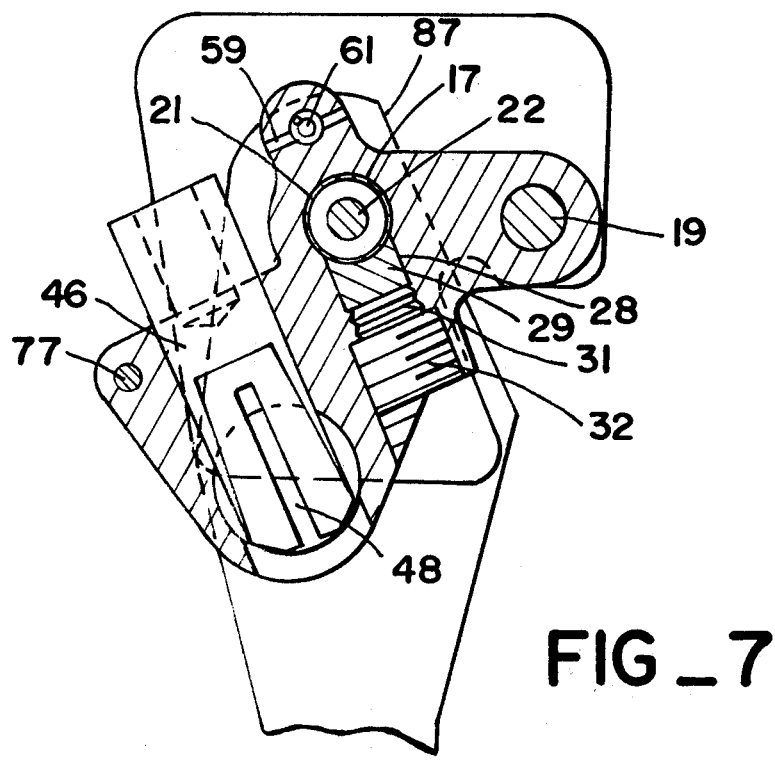
FIG_7

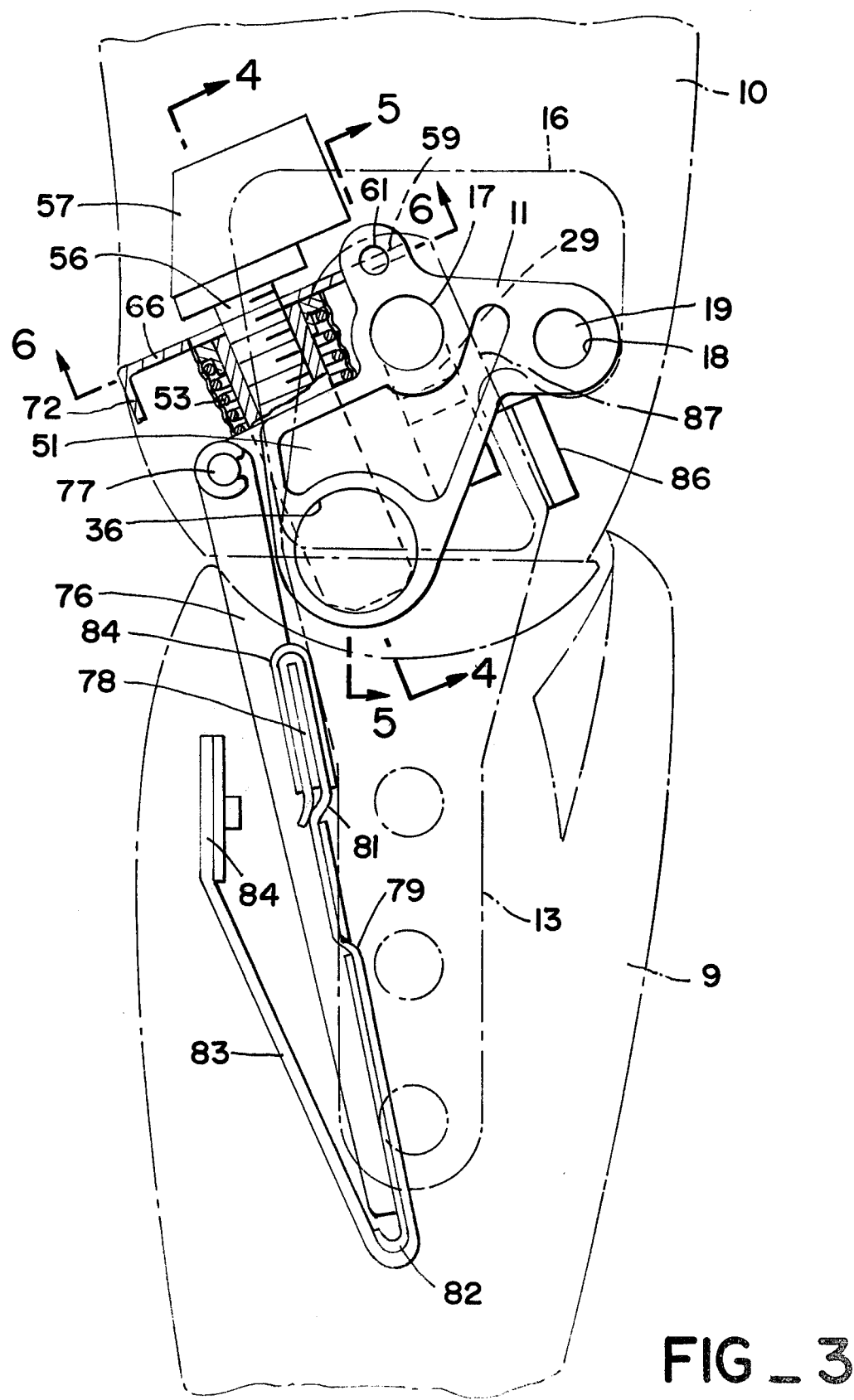
FIG_3

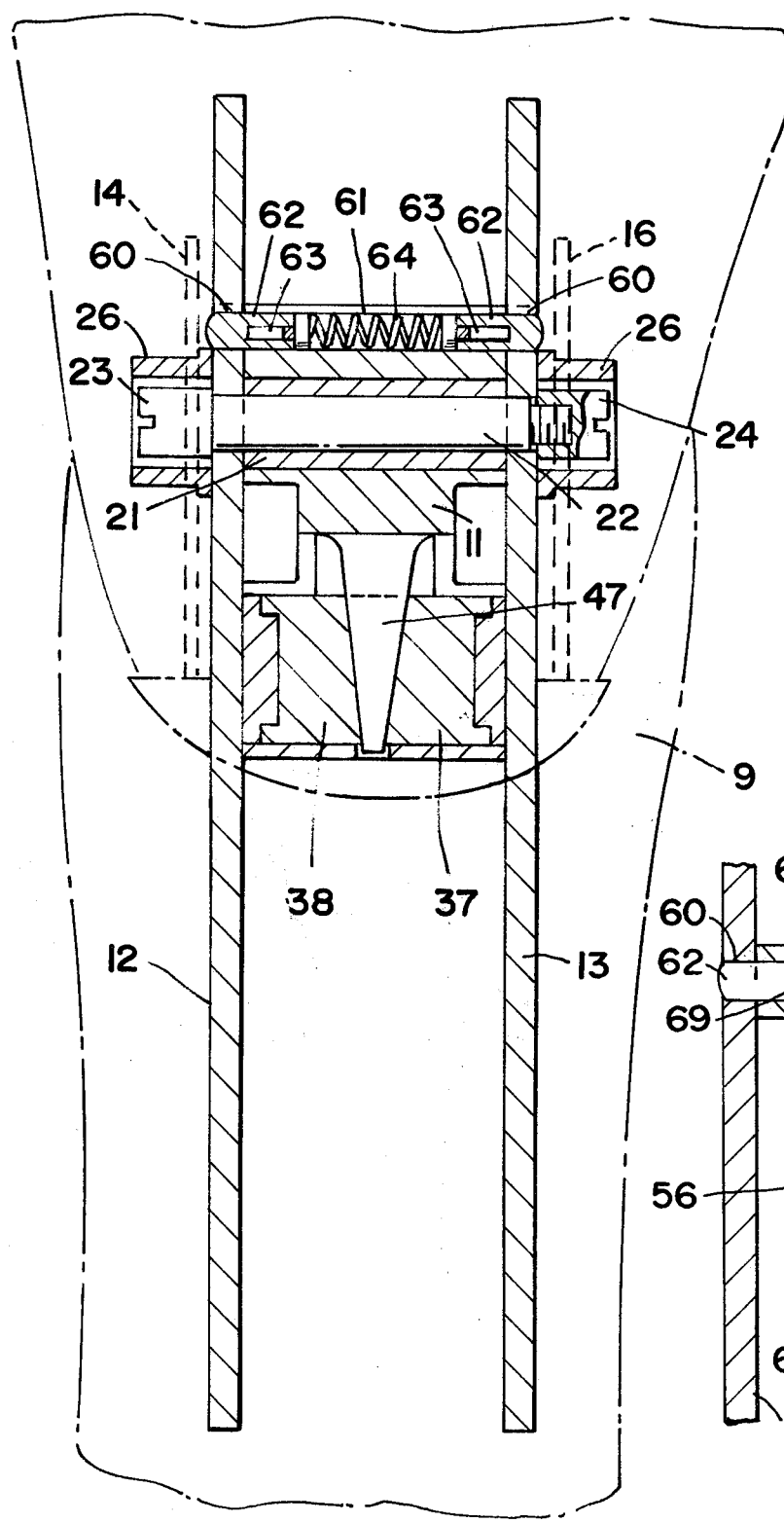
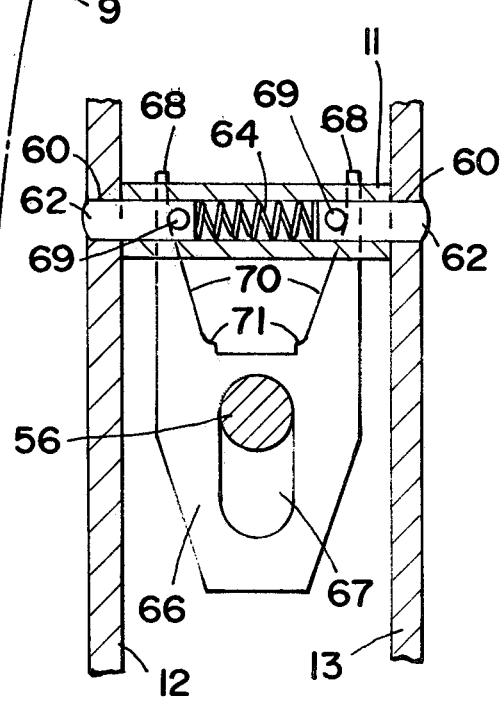
FIG_5
FIG_6

PROSTHETIC KNEE APPARATUS

BACKGROUND OF THE INVENTION

The ultimate goal in the design of a prosthetic knee joint is the duplication of the action of a human knee joint, both in stationary support and in walking. In the past, knee joints have been provided with a single axis pivot to permit angular motion between the femoral and tibial portions of the prosthetic leg. Knee joints have also been provided with locking mechanisms to provide secure support during prolonged standing, to aid an unstable walker, or to provide stability or uneven ground, stairs, and ramps.

The more difficult problem in prosthetic knee design has been the duplication of the knee motion required for walking or striding. One technique known in the prior art has been the provision of a braking device in the knee mechanism which is actuated by weight applied to the knee. The braking mechanism has usually comprised a brake band extending about a brake drum.

The problem often encountered in using this and other forms of braking apparatus is that the brake does not release immediately upon removal of the weight which causes brake actuation. Thus, during a normal walking stride, when the prosthetic leg reaches the posteriormost position and the weight is shifted to the other leg, the prosthetic knee does not immediately pivot freely as it is moved forward to the anterior position. This deficiency in the prior art mechanisms can only be overcome by a pronounced weight shift to the other leg, resulting in an obvious and characteristic limp.

Such a limp is a great deviation from the ideal goal of duplication of the human knee motion. More importantly, the limp is an embarrassment for many prosthetic knee wearers, and it also represents an increased hazard during walking.

SUMMARY OF THE PRESENT INVENTION

The present invention comprises a prosthetic knee apparatus which facilitates a more natural walking motion than that permitted by any prior art device. The knee apparatus includes a novel braking mechanism which operates more positively and releases more quickly than any known in the art, to immobilize the knee with the femoral and tibial portions in any angular relationship.

The invention includes a pair of spaced leg brackets joined at their lower ends to the lower leg prosthesis and pivotally secured at their upper ends to a posterior pivot shaft extending through the knee mechanism housing. The housing itself is disposed between a pair of spaced side brackets which depend from the upper leg prosthesis, and which extend exteriorly adjacent to the leg brackets.

An anterior pivot shaft extends through the side brackets and the knee mechanism housing, as does the posterior pivot shaft. The posterior pivot shaft is provided with some play within the housing, to permit a small degree of rotation about the anterior pivot shaft. The housing is provided with a pair of extendable locking pins which engage holes in the leg brackets to lock the lower leg prosthesis in the fully extended position. The knee mechanism also includes a friction shoe device for dampening the pivotal motion about the posterior pivot shaft, and an extension bias device which resiliently biases the knee prosthesis to the fully extended position.

A unique and important feature of the present invention is the braking device which immobilizes the knee mechanism with the upper and lower leg portions in any angular relationship whenever sufficient weight is applied to the upper leg. The brake mechanism includes a pair of opposed brake cylinders having outer frictional surfaces which impinge on the leg brackets. The inner ends of the brake cylinders are provided with oblique opposed surfaces which are engaged by a wedge member. The wedge member is driven downwardly to engage the brake cylinders by a transverse bracket extending between the side brackets. The transverse bracket descends whenever sufficient weight is applied posteriorly of the anterior pivot shaft, causing the housing to pivot relatively about the interior pivot shaft and bring the wedge member into engagement with the transverse bracket.

A BRIEF DESCRIPTION OF THE DRAWINGS

FIG. 1 is a cut-away perspective view of the knee prosthesis of the present invention.

FIG. 2 is a detailed view of the wedge member of the knee prosthesis of the present invention.

FIG. 3 is a cross-sectional elevation of the knee prosthesis of the present invention.

FIG. 4 is a cross-sectional elevation of the knee prosthesis, taken along line 4—4 of FIG. 3.

FIG. 5 is a cross-sectional elevation of the knee prosthesis, taken along 5—5 of FIG. 3.

FIG. 6 is a cross-sectional view of the locking mechanism of the knee prosthesis, taken along line 6—6 of FIG. 3.

FIG. 7 is a cross-sectional elevation of the housing of the knee prosthesis.

DESCRIPTION OF THE PREFERRED EMBODIMENT

The present invention is generally characterized as a knee prosthesis which joins an upper leg or femoral prosthesis to a lower leg or tibial prosthesis, and which is also adapted to closely mimic the action of a human knee. The invention includes a pair of laterally spaced side brackets 14 and 16 which extend downwardly from the upper leg prosthesis 10, and a pair of laterally spaced leg brackets 12 and 13 which are joined to the lower leg prosthesis 9. As shown in FIG. 5, the upper portions of the leg brackets 12 and 13 are disposed within the side brackets 14 and 16.

The knee prosthesis includes a knee mechanism housing 11, which is generally situated within the confines of the side brackets 14 and 16. The housing 11 includes a laterally extending anterior bore 18, and a laterally extending posterior bore 17. Both of the bores 17 and 18 extend entirely through the housing 11. An anterior pivot shaft 19 is secured in the bore 18 and extends through both the side brackets 16 to join the housing 11 and the side brackets in a pivotal manner.

As shown in FIGS. 5 and 7, a sleeve 21 is secured in the posterior bore 17 by means of a slip-fit therein. The sleeve 21 extends the entire length of the bore 17 with the ends of the sleeve impinging on the inside surfaces of the leg brackets 12 and 13. A hole is provided in each bracket 12 and 13 aligned with the sleeve 21, and a posterior pivot shaft 17 extends therethrough. As shown in FIG. 7, the pivot shaft 22 is substantially smaller in diameter than the inner diameter of the sleeve 21, so that there is some freedom of movement of the shaft 22 within the sleeve.

One end of the shaft 22 is provided with a sloted head 23, and a slotted retaining nut 24 is threadedly secured to the other end of the posterior shaft. The compression of shaft 22 and nut 24 joins the brackets 12 and 13 to the intermediate sleeve 22 to form a rigid assembly thereof. Each of the slotted members 23 and 24 are secured within the bushings 26, and are provided with approximately the same clearance as the shaft 22 within the sleeve 21. Aligned holes in the side brackets 14 and 16 receive the bushings 26 in a press fit manner, as shown in FIG. 5.

It may be appreciated that the leg brackets 12 and 13 are thus pivotally secured to the knee mechanism housing 11. Furthermore, the clearance provided between the shaft 22 and the sleeve 21, and between the slotted end 23 and 24 and the bushings 26 provide a slight freedom of movement between the housing 11 and the side brackets 14 and 16. This freedom of movement permits a limited amount of rotation by the housing 11 about the anterior pivot shaft 19. The significance of this limited rotation about the anterior shaft will be explained in the following.

The knee mechanism of the present invention is also provided with apparatus for applying a selected and variable amount of friction to the posterior pivot. As shown in FIG. 7, the housing 11 is provided with a cylindrical bore 28 which is oriented orthogonally to the bore 17 and is disposed medially within the housing itself. A friction shoe 29 is disposed in the bore 28, and is provided with a concave interior surface which impinges on and mates with the presenting portion of the exterior surface of the sleeve 21. A plurality of belleville washers 31 abuts the exterior end of the shoe 29, and a threaded plug 32 is received within the threaded exterior end of the bore 28 to secure the assembly therein.

It may be appreciated that the threaded plug 32 may be threaded inwardly or outwardly in the bore 28 to selectively vary the force applied to the friction shoe 29. The amount of force applied to the shoe 29 in turn determines the amount of friction which is applied to the exterior of the sleeve 21. Thus the freedom of rotation of the leg brackets 12 and 13 about the posterior pivot may be selectively varied to suit the requirements of the wearer of the prosthesis.

A most salient and unique feature of the knee prosthesis is the provision of a frictional safety lock which immobilizes the lower leg prosthesis at any angular relationship to the upper leg prosthesis. As shown in FIGS. 4 and 7, this feature includes a laterally extending bore 36 in the housing 11, the bore 36 being disposed below and slightly posteriorly of the bore 17. A pair of opposed brake cylinders 37 and 38 are disposed within the bore 36. Joined to the exterior ends of the brake cylinders are brake pads 39 and 41 respectively. The brake cylinders are each provided with a diametrical slot 42 to receive the free ends of a U-shaped retaining spring 43. The spring 43 biases the brake cylinders inwardly and maintains the brake pads 39 and 41 out of frictional engagement with the leg brackets 12 and 13 respectively.

The inner faces of the brake cylinders extend obliquely to define a V-shaped gap therebetween. Also, each of the inner faces of the brake cylinders is provided with a diametrically extending narrow shoulder 44, as also shown in FIG. 2.

A bore 51 extends from the top of the housing 11 obliquely downwardly, opening to the bore 36. Disposed within the bore 51 is a generally cylindrical wedge member 46. As shown in FIG. 2, the upper portion 49 of the wedge member is provided with external threads, and with an internally threaded hole extending into the top end of the wedge member. The lower end 47 of the wedge member is provided with obliquely related planar surfaces which define a wedge having a V-shaped profile, as shown in FIG. 4. A slot 48 extends through the lower portion of the wedge member from one planar surface to the other, and is sufficient in width to slidably engage the diametrical shoulders 44 of the brake cylinders 38 and 37.

It should be noted that the wedge member 46 is freely translatable within the bore 51. As the wedge member descends in the bore toward the orthogonally related bore 36, the action of the lower wedge end 47 on the oblique interior faces of the brake cylinders causes the cylinders to translate divergently and outwardly, the brake surfaces 39 and 41 impinging on the leg brackets 12 and 13 respectively. Sufficient force applied to the wedge member will cause the brake surfaces 39 and 41 to generate enough friction to immobilize the leg brackets with respect to the housing 11. It may be appreciated that this action will occur no matter what the angular relationship of the leg brackets 12 and 13 to the housing 11 may be, so long as the brake pads can impinge on the leg brackets.

As shown in FIG. 4, a nut 52 is threadedly secured to the upper portion 49 of the wedge member which extends out of the bore 51. A helical compression spring 53 is secured between the nut 52 and the exterior surface of the housing 11, to bias the wedge member upwardly and out of engagement with the brake cylinders. A flexible boot 54 is secured about the nut 52 and the spring 53 to prevent any interference therewith.

Secured in the threaded hole in the upper end of the wedge member 46 is a flat head bolt 56. A generally U-shaped actuating bracket 57 is secured between the side brackets 14 and 16, and is adapted to impinge on the bolt 56. The engagement between the bracket 57 and the wedge member may be selectively varied by threading the bolt 56 into or out of the hole in the wedge member. Whenever the actuating bracket 57 impinges on the bolt 56 with sufficient force to overcome the resilient expansive force of the spring 53, the wedge member will be driven to cause the frictional locking action described in the foregoing. The bolt 56 is adjustable to compensate for wear in the wedge member and shoe assembly. It may be appreciated that the nut 52 varies the spring force which must be overcome in order to cause the frictional locking action.

The frictional locking action represents a safety feature of great importance to the wearer of the prosthesis. Whenever a knee flexion movement is initiated by applying weight posteriorly of the anterior pivot shaft 19, the housing 11 pivots clockwise about the anterior pivot shaft with respect to the side brackets which are joined to the upper leg prosthesis. This relative motion between the housing and the side brackets causes the actuating bracket 57 to descend and strike the head of the bolt 56. The frictional locking action will then occur as described. This action of the knee prosthesis prevents the genuflection of the artificial leg so long as weight is applied posteriorly of the anterior pivot shaft. Thus the leg prosthesis cannot suddenly collapse and cause the individual to suffer a dangerous fall.

The knee prosthesis is also provided with a full extension lock for locking the knee in the fully extended position during prolonged periods of standing. The full extension lock includes a bore 61 extending through the housing 11, above and slightly posteriorly of the bore 17, as shown in FIG. 3. A slightly oblique laterally extending slot 59 extends normally through the medial portion of the bore 61 and the housing 11, as shown in FIG. 1. A pair of opposed locking pins 62 are disposed within the bore 61, and a helical compression spring 64 biases the locking pins outwardly. As shown in FIG. 5, the upper ends of the leg brackets 12 and 13 are provided with holes 60 which receive the locking pins 62 when the lower leg prosthesis is in the fully extended position.

Each locking pin 62 includes a longitudinally extending diametrical slot 63 in the inner end thereof. A post 69 extends diametrically through each of the pins 62 adjacent to the inner end thereof and perpendicular to the slot 63. Each post 69 supports a rotatable roller which is disposed within the slot 63.

With reference to FIG. 6, the full extension lock also includes a sliding actuator 66. The actuator includes an elongated guide slot 67 through which the upper shank of the bolt 56 of the frictional locking assembly extends. The actuator 66 is a generally planar member, and is provided with a handle 72 at the outer end thereof. The inner end of the actuator 66 is provided with a pair of tines 68. A shown in FIG. 6, the narrow inner ends of the tines extend through the slot 59 in the housing and also through the slots 63 in the locking pins 60. The confronting edges 70 of the tines 68 coverge as they extend outwardly to form camming surfaces which impinge on the rollers within the slots 63. The outer extremities of the edges 70 are provided with stops 71 to limit the travel of the actuator 66.

It may be understood that with the locking pins 62 disposed within the holes 60 in the leg brackets 12 and 13, the leg brackets cannot pivot about the posterior, pivot axis. Thus the leg is locked in the fully extended position. To release the locking pins, the actuator 66 is manually urged to translate inwardly into the slot 59 in the housing. The locking pin rollers are thus caused to ride on the camming surfaces 70, and the pins 62 are withdrawn into the bore 61. The locking pins are thus withdrawn from the holes 60 in the leg brackets and the leg brackets are free to pivot about the posterior pivot axis. This action also further compresses the spring 64.

The full extension lock may be actuated by manually pulling the slide 66 outwardly. The spring 64 is then free to urge the pins 62 into the holes 60 in locking engagement. The full extension lock may be actuated while the knee is genuflected; in this case, the rounded outer ends of the locking pins 62 will ride on the interior surfaces of the leg brackets 12 and 13 until the lower leg prosthesis is pivotted to the full extension position, and the holes 60 are aligned with the pins 62. Thus, for example, the amputee may actuate the full extension lock while in a sitting position, or similar genuflected repose. Upon standing or otherwise fully extending the leg prosthesis, the leg will automatically lock in the fully extended position.

The knee prosthesis of the present invention also includes an extension bias device which resiliently biases the knee toward a fully extended disposition and prevents heel rise of the lower leg prosthesis. The extension bias device includes a pair of opposed longitudinally extending support members 76 which are pivotally joined to opposed lateral sides of the housing 11 by pivot pin 77. Extending between and joining the members 76 is a web member 78, which is provided with slots 79 and 81 therethrough. The web member 78 is also provided with a rounded lower end 82.

The extension bias device includes an elastic panel 83 which is secured at one end 84 to the upper posterior portion of the lower leg prosthesis 9. The elastic panel 83 is carried around the rounded end 82 of the web member 78 to the anterior side thereof, and is woven through the slots 79 and 81 and about the top edge of the web member 78, as shown in FIG. 3. A spring clip 84 is secured about the upper edge of the web member 78 to retain the other end of the elastic panel thereabout.

Due to the posterior offset of the pivot 77 from the pivot axis 17 of the lower leg, the support members 76 are in effect driven downwardly into the lower leg prosthesis 9 whenever the lower leg is pivotted in the knee assembly. This action causes the elastic panel 83 to stretch and to thereby resiliently bias the lower leg to return to the fully extended position, as shown in FIG. 3. This resilient biasing toward the fully extended position prevents uncontrolled flexion of the knee joint during a normal walking stride.

It should be noted that the extension bias device may be easily adjusted to suit the knees of the wearer of the prosthesis. The spring clip 84 may be easily removed, and the upper end of the elastic panel may be pulled taut or loosened to adjust the degree of elastic force applied to the knee mechanism. The spring clip 84 is then replaced to retain the elastic panel with the desired tension.

The knee mechanism is prevented from pivotting past the fully extended position by means of a stop bracket 86, as shown in FIGS. 1 and 3. The stop bracket is a generally U-shaped member which has its ends secured to the lower anterior portions of the side brackets 14 and 16. The stop bracket 86 is canted obliquely so that it impinges in a flush manner on the anterior upper edge 87 of the leg brackets 12 and 13. The bracket 86 provides a positive stop which is not adjustable and which cannot fail.

From the foregoing description, it may be appreciated that the knee mechanism of the present invention provides many unique features which aid in duplicating the action of the human knee. For example, the frictional locking arrangement, in conjunction with the anterior and posterior pivot shaft system, enables the wearer of the prosthesis to lock the knee in any angular orientation merely by placing sufficient weight posteriorly of the anterior pivot shaft. This feature greatly aids in promoting a natural walking stride, as well as facilitating other movements such as bending, crouching, etc. The unique positively acting full extension lock provides greater ease during extended periods of standing, and provides greater comfort for the prosthetic wearer. Furthermore, the easily adjustable extension bias device enables the wearer of the prosthesis to adjust the elastic bias of the knee to suit his or her needs and activities.

We claim:

1. A knee prosthesis, comprising a pair of spaced side support members depending from an upper leg prosthesis, a knee mechanism housing disposed between said side support members, a pair of spaced leg brackets secured at their lower ends to a lower leg prosthesis, an anterior pivot shaft extending laterally through said housing and through said side support members, a posterior pivot shaft extending laterally through said housing and through said leg brackets, and frictional locking means, actuated by pivotal motion about said anterior pivot shaft, to immobilize said leg brackets with respect to said knee mechanism housing.

2. The knee prosthesis of claim 1, wherein said frictional locking means includes a pair of opposed brake members slidably supported in said housing and disposed to impinge their outer frictional surfaces on said leg brackets.

3. The knee prosthesis of claim 2, wherein the inner ends of said brake members are provided with obliquely extending confronting surfaces defining a V-shaped gap therebetween, and further including wedge means extending into said gap to drive said brake members outwardly to impinge on said leg brackets.

4. The knee prosthesis of claim 3, wherein said wedge means includes a wedge member having a lower tapered portion disposed in said gap.

5. The knee prosthesis of claim 4, further including actuator bracket means extending between side support members for impinging on the upper end of said wedge member and translating said wedge member toward said brake members.

6. The knee prosthesis of claim 5, wherein said posterior pivot shaft includes a clearance means for providing limited translational motion between said knee mechanism housing and said posterior pivot shaft in a direction orthogonal to said posterior pivot shaft.

7. The knee prosthesis of claim 4, wherein said clearance means includes a sleeve extending laterally through said knee mechanism housing, said sleeve having an inner diameter larger than the diameter of said posterior pivot shaft, and wherein said posterior pivot shaft extends concentrically through said sleeve with limited free play.

8. The knee prosthesis of claim 7, wherein said knee mechanism housing is limited in rotation about said anterior pivot shaft by said limited free play of said posterior pivot shaft in said sleeve.

9. The knee prosthesis of claim 4, further including resilient means for biasing said wedge member out of said gap, and adjustment means for adjusting the resilient force of said resilient means.

10. The knee prosthesis of claim 5, further including bolt means extending from said upper end of said wedge member, said actuator bracket means impinging on said bolt means.

11. The knee prosthesis of claim 7, wherein the opposed ends of said posterior pivot shaft extend through said support members with clearance substantially equal to said limited free play of said posterior pivot shaft within said sleeve.

12. The knee prosthesis of claim 1, further including full extension lock means in said housing for releasably immobilizing said upper and lower leg prostheses in a fully extended disposition.

13. The knee prosthesis of claim 12, wherein said full extension lock means includes a laterally extending bore in said knee mechanism housing, and a slot extending diametrically through said bore and through said housing.

14. The knee prosthesis of claim 13, further including a pair of locking pins disposed in said bore, and a detent hole disposed in each of said leg brackets in said fully extended position, said detent holes adapted to receive said locking pins.

15. The knee prosthesis of claim 14, further including spring means for biasing said locking pins outwardly toward said leg brackets, and slide actuator means for selectively withdrawing said locking pins into said bore.

16. The knee prosthesis of claim 15, wherein said slide actuator means includes a pair of spaced tines each extending through said slot and through one of said locking pins in translatable fashion.

17. The knee prosthesis of claim 16, wherein said tines include mutually confronting camming edges which converge from the distal ends of said tines.

18. The knee prosthesis of claim 7, further including friction shoe means disposed in said knee mechanism housing for applying a selectively variable amount of friction to said sleeve.

19. The knee prosthesis of claim 1, further including a leg stop bracket extending between said side support members, the upper forward edges of said leg brackets impinging on said leg stop bracket with said leg brackets in a fully extended position.

20. The knee prosthesis of claim 1, further including extension bias means for resiliently biasing the lower leg prosthesis to a fully extended position.

21. The knee prosthesis of claim 20, wherein said extension bias means includes a bracket pivotally secured at the upper end thereof to a portion of said knee mechanism housing posterior of said posterior pivot shaft.

22. The knee prosthesis of claim 21, further including an elastic web member joined at one end to an upper posterior portion of the lower leg prosthesis, said elastic web member extending downwardly and about the lower distal end of said bracket, the other end of said elastic web member being secured to a medial portion of said bracket.

23. The knee prosthesis of claim 22, wherein said bracket includes a plurality of slots therethrough for receiving said elastic web member therethrough in a weave-like fashion.

* * * * *